US00PP22248P2

(12) United States Plant Patent
Dirr

(10) Patent No.: US PP22,248 P2
(45) Date of Patent: Nov. 15, 2011

(54) ***MAGNOLIA* PLANT NAMED 'CENTENNIAL BLUSH'**

(50) Latin Name: *Magnolia stellata*
Varietal Denomination: Centennial Blush

(75) Inventor: Michael A. Dirr, Bogart, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 12/803,507

(22) Filed: Jun. 29, 2010

(51) Int. Cl.
*A01H 5/00* (2006.01)

(52) U.S. Cl. ..... Plt./223

(58) Field of Classification Search ..... Plt./223
See application file for complete search history.

*Primary Examiner* — Annette Para

(74) *Attorney, Agent, or Firm* — Davis Wright Tremaine LLP

(57) ABSTRACT

A new *Magnolia* plant variety, 'Centennial Blush', is provided. 'Centennial Blush' is a new and distinct cultivar of the plant *Magnolia stellata*, which is characterized by dense conical pyramidal habit, large 12 to 14 cm wide flowers composed of 46 tepals, flower bud development at most nodes resulting in heaviest flowering of any known varieties of *Magnolia stellata*, and ability to set numerous flower buds as a 2 to 3-year-old plant.

3 Drawing Sheets

Latin name of the genus and species of the plant claimed: 'Centennial Blush' is a *Magnolia* plant of the species *Magnolia stellata.*

Variety denomination: The new *Magnolia* plant claimed is of the variety denominated 'Centennial Blush'.

BACKGROUND OF THE INVENTION

The present invention relates to the discovery of a new and distinct cultivar of the plant *Magnolia stellata*, hereafter referred to as 'Centennial Blush', as herein described and illustrated.

The new *Magnolia* plant originated from open-pollinated seed of 'Centennial' (unpatented). The original plant is a conical-pyramidal, full flower plant about 10 years old and 3.6 m by 1.8 m in size. The seedlings were planted in containers and selections were made in March 2010 at former College Station Hydrangea Garden in College Station, Tex.

Asexual reproduction by traditional cuttings has shown that the distinguishing characteristics of this new variety 'Centennial Blush' are stable and reproduced true-to-type in successive generations.

SUMMARY OF THE INVENTION

The new *Magnolia* plant variety 'Centennial Blush' has not been observed under all possible environmental conditions. The phenotype may vary somewhat with variations in environment and cultural practices such as temperature and light intensity without, however, any variance in genotype.

The following traits have been repeatedly observed and are determined to be the distinct characteristics of the new *Magnolia* plant variety 'Centennial Blush':

1. Dense conical pyramidal habit.
2. Large, 12 to 14 cm wide flowers composed of 46 tepals.
3. Flower bud development at most nodes resulting in heaviest flowering of any known varieties of *Magnolia stellata.*

4. Ability to set numerous flower buds as a 2 to 3-year-old plant.

Compared to other varieties of *Magnolia stellata*, the new plant variety 'Centennial Blush' displayed heavier flowering with flower bud development at most nodes. Compared to 'Centennial' (28 to 32 tepals) and 'Lyle's Legacy' (about 29 tepals) per flower, the new variety 'Centennial Blush' had more tepals (46 tepals) per flower.

BRIEF DESCRIPTION OF THE DRAWINGS

The accompanying photographic illustrations show typical specimens of the new variety 'Centennial Blush'. The colors are as nearly true as is reasonably possible in a color representation of this type.

BOTANICAL DESCRIPTION

Figure 1:
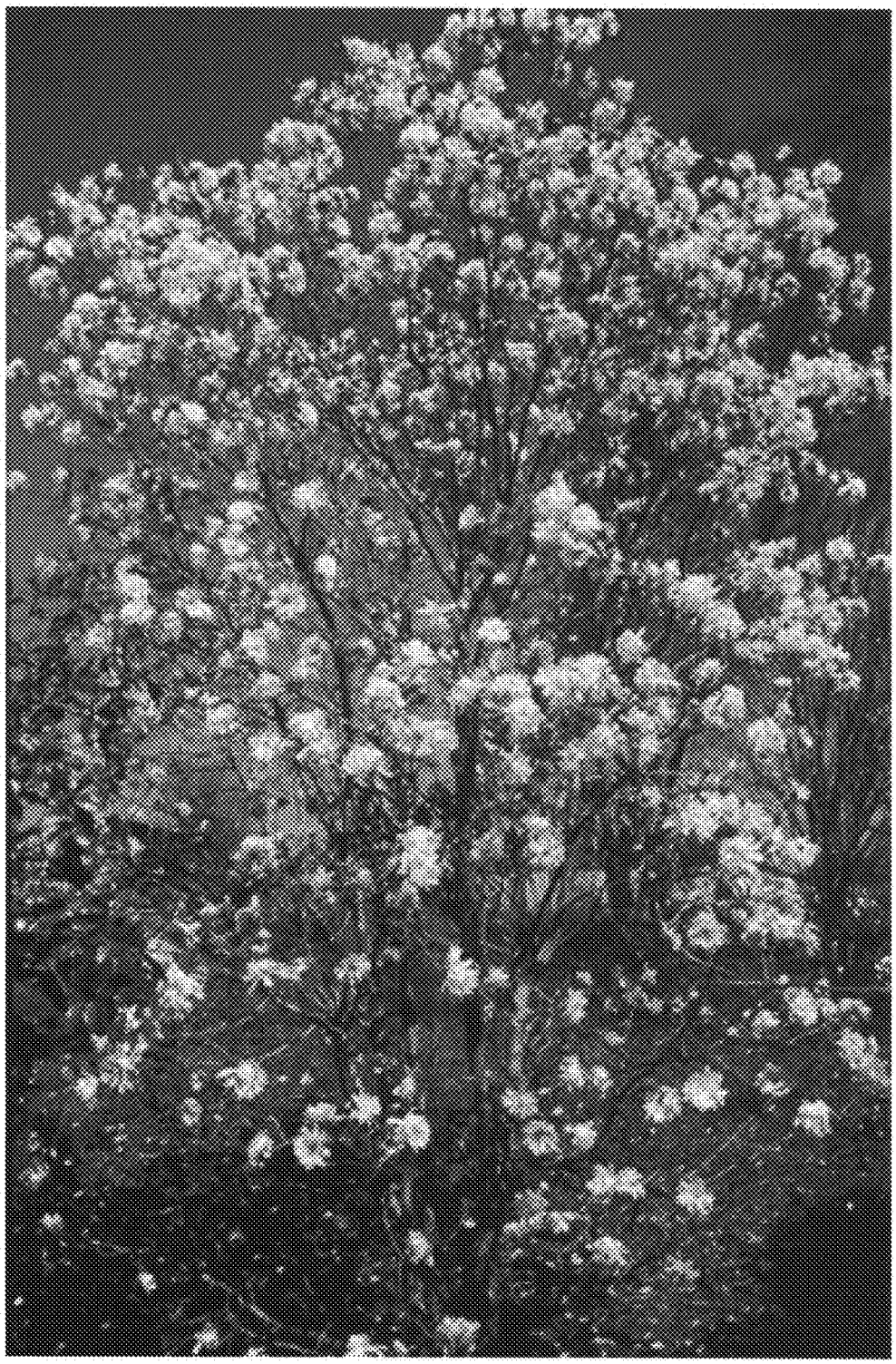
FIG. 1 is a photograph of the new variety 'Centennial Blush'.
Figure 2:
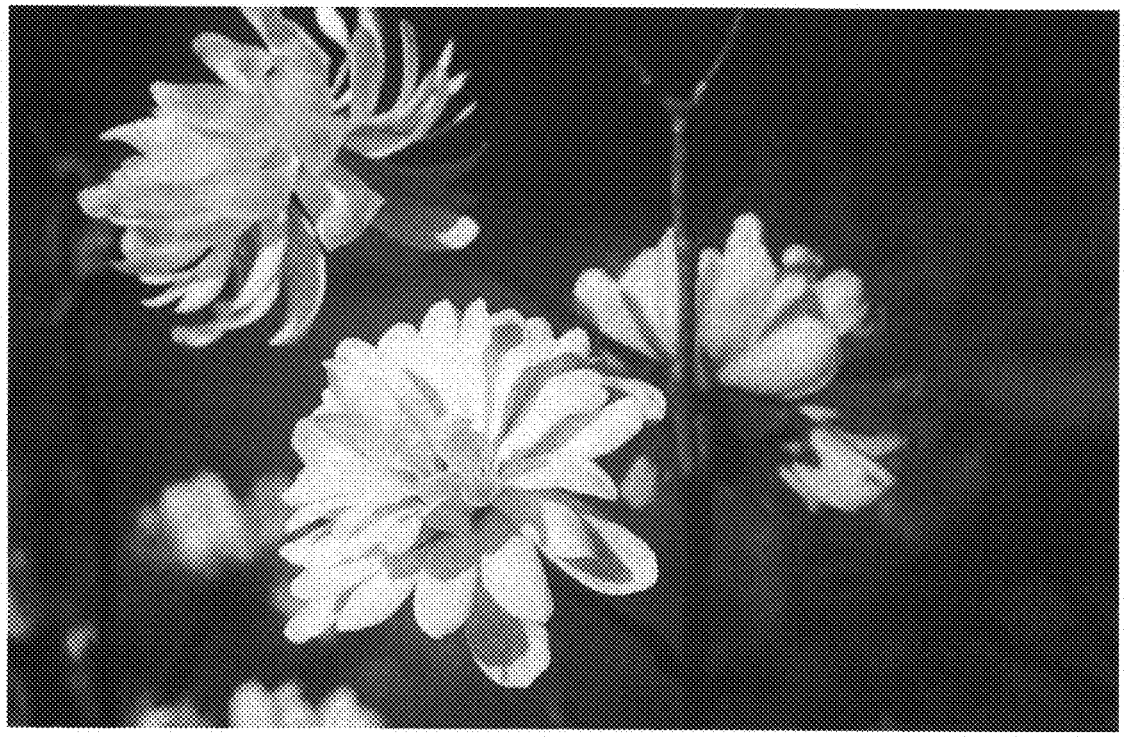
FIG. 2 is a photograph of the flowers of the new variety 'Centennial Blush'.
Figure 3:
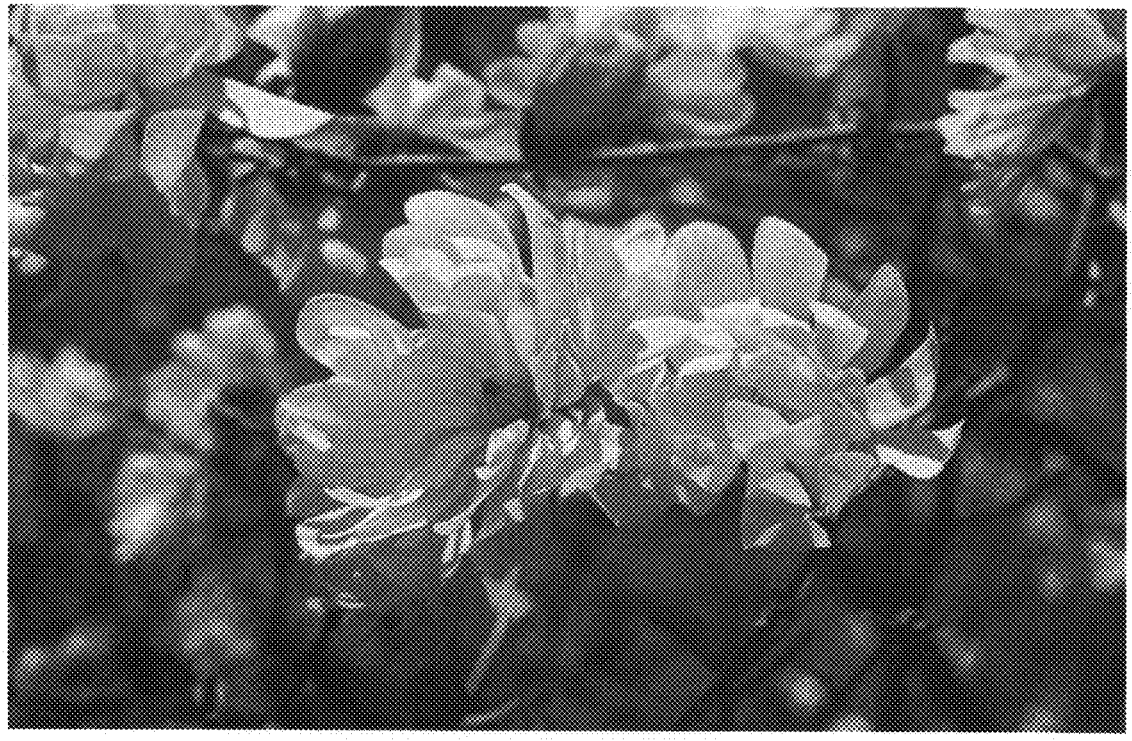
FIG. 3 is a close-up photograph of the flowers of the new variety 'Centennial Blush'.

Throughout this specification, color names beginning with a small letter signify that the name of that color, as used in common speech, is aptly descriptive. Color names beginning with a capital letter designate values based upon The R.H.S. Colour Chart, $5^{th}$ edition published by The Royal Horticultural Society, London, England.

The following is a detailed description of the botanical characteristics of the new variety 'Centennial Blush'. Where dimensions, sizes, colors, and other characteristics are given, it is to be understood that such characteristics are approximations and averages set forth as accurately as practicable. The descriptions reported herein are largely from specimen plants at Watkinsville, Ga. Data were obtained on plants that were 4 years old.

PLANT

Habit: Deuce conical pyramidal.

TRUNK

Color: About Greyed-orange RHS 177D; coated with a moss about Yellow-green RHS 144A.
Diameter: 90 mm.
Texture: Rough.

STEMS

First year: Color: About Brown RHS 200B. Diameter: 2 mm. Pubescence: None; Gray waxiness. Exfoliation: None. Shape: Round. Pith: Type: Solid. Diameter: 2 mm. Color: About White RHS 155A. Odor: None. Lenticels: Number: 10 to 15. Shape: Linear-rounded. Size: 1 to 2 mm long, ½ mm wide. Color: Orange-white RHS 159C. Orientation: Vertical. Internode length: 3 to 4 cm.
Second Year: Color: About Greyed-orange RHS 165A. Diameter: 3 mm. Exfoliation: None; Presence of gray glaucous waxiness.

VEGETATIVE BUDS

Arrangement: Alternate.
Type: Single scale; stalked.
Size:
Average at maturity:
*Length.*—Approximately 15 to 17 mm.
*Width.*—Approximately 6 to 8 mm.
Scale number: 1.
Scale color: About Yellow-green RHS 152A.
Position/disposition: Flat against stem; appressed.
Number at node: Vegetative; 1.
Pubescence: Densely wooly pubescent; About White RHS 155C and about Greyed-brown RHS N199C.
Shape: Elliptical; ovoid.

LEAF SCAR

Shape: Heart-shaped.
Vascular bundle traces: 3.
Pubescence: None.
Position of bud: Sits on top.
Color differentiation: About Green-yellow RHS 161D.
Size:
*Height.*—Approximately 1 mm.
*Width.*—Approximately 4 mm.

TRUNK OR LARGE STEMS

First year:
*Color.*—About Brown RHS 200B.
*Diameter.*—Approximately 2 mm.
*Pubescence.*—None; Grey waxiness.
*Exfoliation.*—None.
*Shape.*—Round.
*Pith.*—Type: Solid. Diameter: Approximately 2 mm. Color: About White 155A.
*Odor.*—None.
*Lenticels.*—Number: 10 to 15. Shape: Linear-rounded. Size: Length: Approximately 1 to 2 mm. Width: Approximately 0.5 mm. Color: About Orange-white RHS 159C. Orientation: Vertical.
Internode length: Approximately 30 to 40 mm.
Second year:
*Color.*—Greyed-orange RHS 165A.
*Diameter*—Approximately 3 mm.
*Exfoliation.*—None; presence of gray glaucous waxiness.

LEAF

Color at emergence: Upper: About Yellow-green RHS 144A. Lower: About Yellow-green RHS 144A. Emerging leaves are very translucent.
Color during summer season:
*Upper.*—About Green RHS 137B.
*Lower.*—About Green RHS 138B.
Blade size:
*Length.*—Approximately 10 to 15 mm.
*Width.*—Approximately 3 to 5 mm.
Apex: Sub-acute to rounded.
Base: Cunerae.
Margin: Entire.
Shape: Elliptical-spatulate.
Veins: 12 to 15 per side; deeply impressed mid vein.
Pubescence: Glabrous on both surfaces.

PETIOLE

Length: Approximately 3.5 mm.
Color: About Green RHS 138B.
Pubescence: Glabrous.

FLOWER BUDS

Size: Early: Length: Approximately 1.9 cm. Width: Approximately 1 cm. At opening: Length: Approximately 3 cm. Width: Approximately 1.5 cm.
Color: Early: About Yellow-green RHS 146B. At opening: About Yellow-green RHS 152B.
Hair color: Early: About White RHS 155C. At opening: About White RHS 155C.
Shape: Ovoid.
Pubescence: Densely silky fine pubescent; About White RHS 155C and about Greyed-brown 199A.

FLOWER

Inflorescences:
Type: Simple.
Size:
*Length.*—Approximately 11 cm.
*Width.*—Approximately 11 cm.
Size of fully open flower: Approximately 12 to 14 cm across.
Color at emergence: About Purple RHS 77B.
Color at full bloom: About Red-purple RHS 69D with a stripe of Purple RHS 77B.
Color at fading: About Greyed-brown RHS N199D at senescence.
Peduncle:
*Color.*—About Greyed-green RHS 195A.
Number of individual flowers per inflorescence: 1.
Fragrance: Fragrant at full bloom.
Tepals:
Number per flower: Average: 46; Varying from 38 to 56.
Size:
*Length.*—46 to 55 mm; Average: 47 mm.
*Width.*—8 to 17 mm; Average: 11 mm.

Shape: Strap-shaped (oblanceolate); concave near apex; broadest above the middle; each tepal with a long extended triangular bar.
Apex: Obtuse.
Base: Acute.
Margin: Entire.
Pubescence: None.
Texture: Waxy; smooth.
Color at peak of bloom:
*Upper surface.*—About White RHS N155B.
*Lower surface.*—About Red-purple RHS 69D with a stripe of Purple RHS 77B.
Corolla:
Color: Deepest colored at base; lighter colored and narrowing to a thin pencil-thick line at apex.
*Exterior color.*—Base: About Red-purple RHS 70B. Tip: About Purple RHS 75B.
*Interior color.*—About White RHS 155D.

MALE REPRODUCTIVE STRUCTURES

Number per flower: 32, 31, 40, 33.
Color:
*Upper surface.*—Top: Yellow-white RHS 158A. Base: Purple RHS 75D.
*Lower surface.*—Top: Yellow-white RHS 158A. Base: Red-purple RHS 70A.
Size:
*Length.*—8 to 10 mm.
*Width.*—1 to 2 mm.
Stamen:
Number: 55.
Shape: Linear with curve.
Color:
*Exterior.*—Top: About Greyed-white RHS 152. Base: About Greyed-purple RHS 72B.
*Interior.*—About Greyed-white RHS 155C.
Size: Length: 0.8 to 1.0 cm. Width: 0.1 to 0.15 cm.

FEMALE REPRODUCTIVE STRUCTURES Pistil

Number: 40 to 50.
Size: Approximately 13 mm in length.
Gynoecium:
Size:
*Length.*—Approximately 2 cm.
*Width.*—Approximately 1 cm.
Stigma:
Color: About Red-purple RHS 63A at tip.
Style:
Color: About Yellow-green RHS 149D.
Ovary:
Color: About Yellow-green RHS 144C.

What is claimed is:

1. A new and distinct variety of *Magnolia stellata* plant named 'Centennial Blush', substantially as illustrated and described herein.

* * * * *

UNITED STATES PATENT AND TRADEMARK OFFICE

CERTIFICATE OF CORRECTION

PATENT NO. : PP22,248 P2
APPLICATION NO. : 12/803507
DATED : November 15, 2011
INVENTOR(S) : Michael A. Dirr It is certified that error appears in the above-identified patent and that said Letters Patent is hereby corrected as shown below:

Column 1, line 19; delete "College Station, Tex" and insert --Athens, Georgia--.

Signed and Sealed this
Seventeenth Day of April, 2012

David J. Kappos

David J. Kappos
*Director of the United States Patent and Trademark Office*